United States Patent [19]

Matsumura et al.

[11] 4,421,391
[45] Dec. 20, 1983

[54] AUTO EYE-REFRACTOMETER

[75] Inventors: Isao Matsumura, Yokosuka; Yasuyuki Ishikawa, Kawaguchi; Reiji Hirano, Yokohama; Shigeo Maruyama, Machida; Yoshimi Kohayakawa, Yokohama, all of Japan

[73] Assignee: Canon Kabushiki Kaisha, Tokyo, Japan

[21] Appl. No.: 191,003

[22] Filed: Sep. 26, 1980

[30] Foreign Application Priority Data

Oct. 5, 1979 [JP] Japan .................. 54-128751

[51] Int. Cl.³ .............................. A61B 3/10
[52] U.S. Cl. .................. 351/211; 351/237
[58] Field of Search .......... 351/6, 13, 14, 124, 351/125, 205, 206, 207, 211, 221, 237; 350/17, 415

[56] References Cited

U.S. PATENT DOCUMENTS

| | | | |
|---|---|---|---|
| 3,594,071 | 7/1971 | Okajima | 351/7 |
| 3,883,230 | 5/1975 | Guilino | 356/124 |
| 4,132,466 | 1/1979 | Matsumura | 351/14 |
| 4,265,518 | 5/1981 | Matsumura | 351/13 |
| 4,293,198 | 10/1981 | Kohayakawa et al. | 351/13 |

FOREIGN PATENT DOCUMENTS 404235  6/1966  Switzerland .................. 351/6

*Primary Examiner*—R. A. Rosenberger
*Attorney, Agent, or Firm*—Fitzpatrick, Cella, Harper & Scinto

[57] ABSTRACT

An eye-refractometer includes an objective optic having a first optical path, an apertured mirror for dividing the first optical path into a second optical path and a third optical path, a mask disposed in the second optical path and having linear marks orientated in at least three directions, a radiation source for illuminating the mask, a mask disposed in the third optical path and having liner detecting areas orientated in at least three directions and photocells arranged behind the respective areas. Improvements in this eye-refractometer comprise an apertured plate disposed between the apertured mirror and one of above said masks and an annular apertured plate disposed between said apertured mirror and the other mask. Another improvement is found in that the length of the linear detecting area is shorter than the length of optimum focused images of the linear marks.

9 Claims, 10 Drawing Figures

AUTO EYE-REFRACTOMETER

BACKGROUND OF THE INVENTION

1. Field of the Invention

The present invention relates to apparatus for automatically measuring the spherical refractive power and astigmatism of eyes.

2. Description of the Prior Art

Refractometry is essential for early detection of trouble in eyes and preparation of corrective lens. There is an increasing demand for apparatus which enables measurement of eye refractive power with higher accuracy and speeds.

Various types of automatic eye-refractometers have already been proposed to satisfy the requirements mentioned above and some of them are already known in the art. See, for example, U.S. Pat. Nos. 3,819,256 and 4,021,102 and Japanese Patent Application laid open Nos. 52,893/1979 and 77,495/1979 (U.S. Application Ser. No. 944,304, now U.S. Pat. No. 4,293,198, issued Oct. 6, 1981). (Among them, the last-mentioned three prior inventions have direct relevance to the subject of the present invention. According to the prior inventions, measuring marks extending in three different directions are projected through the pupil onto the fundus of an eye to be examined and the images of the marks reflected from the fundus are detected relative to three meridians to measure the refractive power of the eye. Spherical visibility, degree of astigmatism and axis of astigmatism of the examined eye are found from the measured result employing the general formula of refractive power, $y = a \sin(2\theta + \zeta) + b$.

Since, as is well-known to those skilled in the art, the reflecting power of fundus is very low, the reflected light from the fundus is very weak as compared with the incident light. Therefore, the accuracy of measurement using such reflected light is greatly affected by noise.

Light reflected upon the cornea constitutes a source of such noise. If the reflected light from the cornea is mixed into the measuring light reflected by the fundus, the measuring accuracy is remarkedly reduced thereby. Therefore, it is desirable to exclude the light reflected from the cornea. The accuracy of measurement is reduced also by change in size of the pupil of the optical system of the refractometer. The size of the pupil may change during power adjusting (focusing). U.S. Ser. Nos. 65,004 now U.S. Pat. No. 4,318,585; 75,115 now U.S. Pat. No. 4,372,655 and 131,499, now U.S. Pat. No. 4,376,573 have proposed a solution to this problem.

In some embodiments described in the aforementioned prior applications, the refractive power of the examined eye is measured by detecting the displacements of images of three target marks reflected from the fundus of the eye. To successfully carry out the measurement, the areas on the cornea of the subject eye through which the target mark constituting beams pass respectively, have to be separated from each other to prevent mutual interference of respective detected information. Therefore, the individual area through which one target mark beam passes is reduced to the extent that insufficient light is reflected from the fundus. Also, as another disadvantage of the prior art devices, the inventors of the present invention have found that when a linearly elongated target mark is projected upon a fundus and an image of the target reflected from the fundus is detected, the target mark image is deformed at both of its ends due to the astigmatism of the examined eye and there is caused thereby a detection error the degree of which corresponds to the degree of the astigmatism.

SUMMARY OF THE INVENTION

Accordingly, it is an object of the present invention to prevent the measuring accuracy of a device constructed in accordance therewith from being reduced by any desirable light falling upon the measuring part thereof.

It is another object of the invention to broaden the area on the cornea through which the beam projected toward the fundus passes as well as the area on the cornea through which the beam reflected from the fundus passes.

It is a further object of the invention to eliminate any adverse effect on measurement resulting from deformation of target mark image caused by the astigmatism of the examined eye.

To obtain the objects according to the invention there is provided an automatic eye-refractometer as set forth in claims. According to one feature of the invention, the beams emerging from target marks and corresponding to three or more meridians are all projected upon the fundus of an eye to be examined, passing through the central part of the cornea and the reflected beams from the fundus are reclined from an annular part of the cornea. This feature enables measurement of the refractive power from blurred images of target marks while excluding harmful reflections from the cornea.

According to another feature of the invention, two ends of a photodetecting area are cut down as compared with the ends of an optimum focused image. This feature excludes the deformed ends of the target mark image from the photodetecting area so as to prevent overlapping of the end area deformed by astigmatism and the photodetecting area.

These and further objects, features and advantages of the invention will appear more fully from the following description taken in connection with the accompanying drawings.

DESCRIPTION OF PREFERRED EMBODIMENTS

Figure 1:
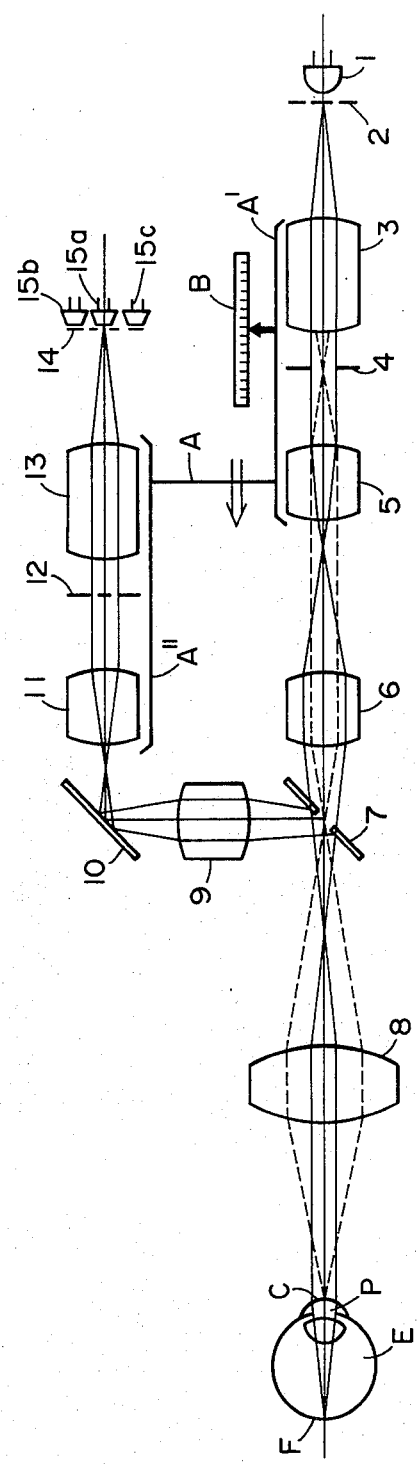
FIG. 1 is a schematic view of an optical system showing an embodiment of the invention.
Figure 2:
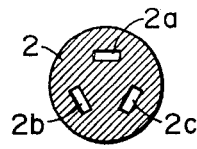
FIGS. 2 to 6 are plan views of the components thereof.

In FIG. 1 showing an embodiment of the invention, E designates an eye to be examined which is at a certain predetermined working distance from an objective lens 8. F is the fundus of the eye, C is the cornea and P is the iris thereof. Designated by 1 is an illumination source which is preferably a light emitting diode. 2 is a measuring mask having three rectangular slits 2a, 2b and 2c formed therein as shown in FIG. 2. The three slits are equally spaced from the optical axis and normal to three meridians respectively. While in the embodiment shown one slit is provided on one meridian, two or more parallel slits may be provided on one meridian. The center of the three meridians corresponds to the optical axis. The number of meridians to be used for measurement is not limited to three and may be increased to further improve the accuracy of measurement.

Figure 3:
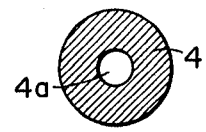

Designated by 3 is a projection lens and 4 is a beam limiting mask. As shown in FIG. 3, the beam limiting mask 4 has an aperture 4a on the optical axis formed therein. 5 is a movable relay lens. The relay lens 5, projection lens 3 and mask 4 are fixed on a lens tube A' in such manner that the focal planes of lenses 5 and 3 are coincident to each other and the mask 4 lies on the focal plane. The lens tube A' is supported movably in the direction of optical axis. Thus, the projection lens 3 and the relay lens 5 constitute an afocal lens group.

Figure 4:
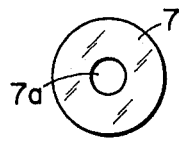
Figure 5:
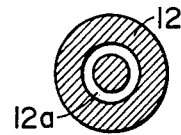

Designated by 6 is a first stationary relay lens and 7 is an apertured mirror. As shown in FIG. 4, the apertured mirror 7 has an aperture 7a formed therein on the optical axis. The aperture 7a lies in the focal plane of the stationary relay lens 6. The cornea C or pupil P is conjugate with the aperture 7a relative to an objective lens 8. 9 is a second stationary relay lens whose focal plane lies in the same plane in which the aperture 7a of the mirror 7 lies. 10 is a mirror provided to change the direction of the optical path from relay lens 9. 11 is a second movable relay lens and 12 is a beam limiting mask. The mask 12 has an annular slit opening 12a whose center lies on the optical axis as shown in FIG. 5.

Designated by 13 is an image receiving lens fixed on another lens tube A''. The relay lens 11 and the mask 12 are also fixed on the lens tube A'' and disposed in such manner that the focal plane of the relay lens 11 is coincident with that of the image receiving lens 13 and the mask 12 lies in the focal plane. The lenses 13 and 11 constitute an afocal lens group.

In the embodiment shown, all of the projection lens' image receiving lens 13 and two relay lenses 5 and 11 are of positive power. However, it is possible to use lenses of negative power as the projection lens, image receiving lens and also the two relay lenses. The beam limiting mask 12 is a composite of a shade point on the optical axis and an aperture stop.

The annular slit 12a of the mask 12 is so measured as to have an outer diameter smaller than the diameter of a pupil image as projected on the mask through the lenses 8, 9 and 11. As the diameter of the pupil image, such diameter should be that of the pupil when contracted by the ambient light in the measuring room. The inner diameter of the annular slit opening 12a is so measured as to be a little larger than an image of the aperture 7a as formed when the aperture 7a of the apertured mirror 7 is projected on the mask 12 through the lenses 9 and 11. The diameter of the aperture 7a is so measured as to be equal to or a little larger than an image of the opening 4a of the beam limiting mask 4 as formed when the opening 4a is projected on the apertured mirror 7 through the lenses 5 and 6. Considering a beam of light emerging from the opening 7a of the apertured mirror 7 on which an image of the pupil is formed, the relation between lenses 5 and 6 and between lenses 9 and 11 is afocal and therefore the size and position of the pupil remains constant even when the lens 5 or the lens 11 is moved. On the other hand, the distance of movement the projection side lens group (3, 5) can be made equal to that of the receiving side lens group (11, 13) by making the focal distances equal to each other as to the projection lens 3 and image receiving lens 13, stationary relay lenses 6 and 9 and movable relay lenses 5 and 11.

Figure 6:
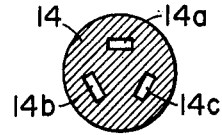

Designated by 14 is a detecting mask having therein three rectangular slits. As shown in FIG. 6, the three slits 14a, 14b and 14c are arranged equally distant from the optical axis and normal to three meridians respectively. Photoreceptor elements 15a, 15b, and 15c are provided to receive the respective beams passing through the detecting slits 14a, 14b and 14c. The lens tubes A' and A'' mentioned above are connected with each other by an arm A which can be moved in the direction of the double-lined arrow by suitable driving means (not shown). B is a position detector which may be, for example, a linear encoder. The position detector B serves to detect the position on the optical axis of the lens groups. The position has a direct relation to the refractive power to be measured.

The manner of operation of the apparatus is as follows:

During one measuring operation, the arm A is moved from a remote point to a near point or vice versa at a uniform speed one time for power adjustment. At a certain point in time during this movement of the arm A, the measuring mask 2 and fundus F and also the detecting mask 14 and fundus F become conjugated. If the examined eye has some astigmatism, then the meridians can not become conjugated at the same time and separate points at which conjugation occurs will be detected. By turning on the illumination source 1, the respective slits 2a, 2b and 2c of the measuring mask 2 are illuminated and the beams of light emerging from the respective slits 2a, 2b and 2c are directed toward the projection lens 3 (conjugated relation is indicated by the solid lines in FIG. 1). The beams are once focused by the projection lens 3 and movable relay lens 5 and then again focused after passing through the apertured mirror 7. Thereafter, the beams are projected onto the fundus F through the objective lens 8. In this course, the aperture 4a of beam limiting mask 4 limits all the beams to be projected on the fundus. Under the action of movable and stationary relay lenses 5 and 6, an image of aperture 4a (its conjugated relation is indicated by the broken lines) is formed in the aperture 7a of the apertured mirror 7 and then formed in the vicinity of the pupil by the action of objective lens 8. Therefore, areas on the cornea or pupil which the projection beams pass through are limited accordingly.

If the fundus and the measuring mask are conjugated, then there will be formed clear and sharp images of the respective slits 2a, 2b and 2c on the fundus F. The beams scatter reflected therefrom project toward the objective lens 8 which focuses the beams. After being focused by the objective lens, the beams are reflected by the mirror surface of the apertured mirror 7 and then refocused by the stationary relay lens 9. The mirror 10 directs the reflected beams from the fundus toward the movable relay lens 11. The relay lens 11 and the image receiving lens 13 make the beams form slit images on the detecting mask 14. Those beams pass through the slits 14a, 14b and 14c and are received by the photoreceptor elements 15a, 15b and 15c, respectively. Here, it should be noted that only a limited beam can pass through the slit opening 12a of the beam limiting mask 12. Assuming that the mask 12 is projected on the pupil, an image of the slit opening will be formed on a certain limited area of the pupil. The above mentioned limited beam which can pass through the slit opening 12a is the beam which passed through the limited area. In this manner, mixing of any portion of the reflected beam from the cornea into the reflected beams from the fundus can be prevented completely in this arrangement.

Figure 7:
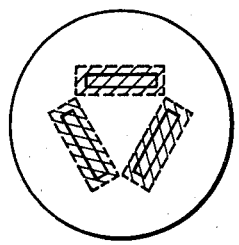
FIGS. 7 and 8 show images of measuring slits on a detecting mask.
Figure 8:
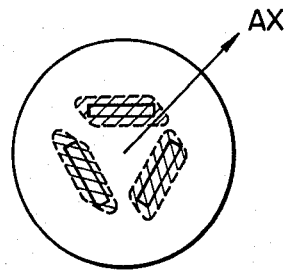

The point in time at which the fundus and the mask become conjugated and of which description has been made above, occurs only once during scanning of the lens groups. At all of the remaining points in time there are formed on the fundus, and therefore on the detecting mask, those slit images which are more or less blurred as shown in FIGS. 7 and 8 showing examples of blurred slit images formed on the detecting mask, the rectangles described by solid line indicate real forms of the detecting slits and hatched areas indicate blurred slit images then formed. FIG. 7 is for a examined eye which has no astigmatism and FIG. 8 is for another tested eye which has astigmatism. The slit images shown in FIG. 8 have somewhat deformed forms as compared with those in FIG. 7. AX in FIG. 8 indicates the axis of astigmatism.

As a matter of course, when the images of the measuring slits are blurred as shown in FIGS. 7 and 8, the quantity of light passing through the detecting slits is reduced as compared with the above-described conjugated case wherein sharp and clear slit images were formed on the detecting mask. This means that the point in time at which the fundus and the slits of the measuring mask become conjugated can be detected by measuring the quantity of light passing through the detecting slits.

In general, the refractive power $P\theta$ on a meridian having an inclination $\theta$ to the strong principal meridian can be represented by the following equation:

$$P\theta = Ph \sin^2\theta + Pe \cos^2\theta$$

Wherein,

Ph is refractive power in the direction of strong principal meridian, and

Pe is refractive power in the direction of weak principal meridian.

The refractive power in the direction is determined by the movement of the measuring meridian.

Therefore, as disclosed in Japanese Patent Application laid open No. 77,495/1979 (U.S. patent application Ser. No. 944,304, and now U.S. Pat. No. 4,293,198, issued Oct. 6, 1981), spherical visibility, degree of astigmatism and axis of astigmatism can be found by calculating from the position of the moving lens groups found at the point in time when a peak is detected in the electrical outputs from the photoreceptor 15a, 15b, 15c which receive beams of light passing through the slits 14a, 14b, 14c, respectively.

In the embodiment shown, the slits 2a, 2b, 2c of the mask 2 and the slits 14a, 14b, 14c of the mask 14 are disposed conjugated with each other relative to the fundus of eye. Under the condition, as seen in FIGS. 7 and 8, the formed images are blurred not only in the direction of the measuring meridian but also in the direction normal thereto. In particular when the tested eye is astigmatic as in the case of FIG. 8, the individual slit images have different deformations one to another due to the effect of the astigmatism of the eye. Namely, the astigmatism makes the slit images deform differently because each of the slit images is a resultant of deformed image components in the direction of the meridian and in the direction of the astigmatic axis AX.

For high accuracy of measuring it is desired to minimize the above effect. This object can be obtained by excluding both end portions of the most deformed slit image from the measuring area. More particularly, the length of slits 14a, 14b, 14c of the mask 14 measured in the direction normal to the measuring meridian is preliminarily cut down as compared with that of the sharp and clear images of slits 2a, 2b, 2c of the mask 2 reflected from the fundus.

Obviously many modifications and variations of the present invention are possible in the light of the above teachings. In the above embodiment, the lens groups on the projection side and on the image receiving side have been moved. However, as a modification thereof, it is also possible to move a first unit including the measuring mask and the illumination source and a second unit including the detecting mask and the photo receptors while holding a particular correlation between the two units. Also, the movable lens group may be constituted differently from the above embodiment.

Furthermore, while in the above embodiment the beam limiting masks 4 and 12 have been shown to be moved together with the corresponding afocal lens groups, the beam limiting masks 4 and 12 may be disposed fixed while the afocal lens groups are disposed between the objective lens 8 and the apertured mirror 7.

As another modification of the above embodiment, the photoreceptor elements may be arranged behind the measuring mask and the illumination source may be positioned behind the detecting mask. In this modification, the projection side and the light receiving side are reversed to those in the above embodiment. Thus, it is possible to project light on the fundus of an examined eye through the annulus part thereof and receive the reflected light from the fundus through the center part thereof.

Figure 9:
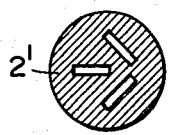
FIGS. 9 and 10 show modifications of the mask used in the invention.
Figure 10:

By employing such a type of measuring system in which blurring of formed images is detected there is obtained relatively broad freedom regarding the arrangement of slits on the measuring mask. The mask 2' shown in FIG. 9 is a modification of the mask 2 shown in FIG. 2 and used in the above embodiment. FIG. 10 shows one form of a mask useful for measuring of five meridians.

It will be understood by those skilled in the art that the foregoing and other changes in form and details can be made without departing from the spirit and scope of the invention.

What we claim is:

1. An auto eye-refractometer comprising:

marking means for forming linear marks orientated in at least three directions;

projection optical means for projecting the measuring beams emerging from said linear marks onto the fundus of an eye to be examined and having a projecting optical path;

first adjusting means disposed on said projecting optical path to move images of said linear marks along said projecting optical path;

receiving optical means for receiving the measuring beams emerging from said linear marks reflected from the fundus and having a receiving optical path;

detecting means having linear detecting areas for detecting each of the measuring beams passed through said receiving optical means;

second adjusting means disposed on said receiving optical path to focus the measuring beams on said linear detecting areas;

first beam limiting means disposed in said projecting optical path to limit the beams and having a light transmitting area provided on the optical axis; and second beam limiting means disposed in said receiving optical path to limit the beams and having a light shading area provided on the optical axis.

2. An auto eye-refractometer according to claim 1 wherein said first beam limiting means is a plate having an aperture therein and said second beam limiting means is a plate having an annular aperture therein.

3. An auto eye-refractometer according to claim 1 wherein said light transmitting area and said light shading area are disposed optically conjugated with the anterior portion of the eye.

4. An auto eye-refractometer according to claim 1 wherein said first adjusting means comprises a first afocal lens group movable along said projection optical path and said second adjusting means comprises a second afocal lens group movable along said receiving optical path and wherein said first beam limiting means is connected with said first afocal lens groups and said second beam limiting means is connected with said second afocal lens group.

5. An auto eye-refractometer according to claim 1 wherein said projecting and receiving optical paths are connected by an apertured mirror having an opening through which the measuring beams pass and wherein said first adjusting means comprises a first afocal lens group movable along said projecting optical path in the region between said apertured mirror and said marking means and said first beam limiting means is connected with said first afocal lens group and wherein said second adjusting means comprises a second afocal lens group movable along said receiving optical path in the region between said apertured mirror and said detecting means and said second beam limiting means is connected with said second afocal lens group.

6. An auto eye-refractometer according to claim 5 wherein said first beam limiting means is a plate having an aperture therein and said second beam limiting means is a plate having an annular aperture therein.

7. An auto eye-refractometer according to claim 1 wherein said linear detecting area is so measured as to be shorter than the length of the linear mark image optimumly focused on said detecting means.

8. An auto eye-refractometer according to claim 1 wherein said detecting means comprises a mask having light transmiting areas orientated in at least three directions and at least three photoreceptors.

9. An auto eye-refractometer comprising:
a projection system for projecting images of rectangular target marks orientated in at least three directions upon different locations of the fundus of an eye to be examined and having means for moving said images of said target marks in the direction of the optical axis;
a detection system for receiving the target mark images reflected from the fundus and including photodetecting means having rectangular photodetecting areas; and means for refocusing the target mark images on the surface of said photodetecting means; a mirror for optically coupling said projection system with said detection system and having an aperture on the optical axis;
a first plate having an aperture therein movable along the optical axis by said moving means; and
a second plate having an annular aperture therein movable along the optical axis by said refocusing means;
the length of said photodetecting areas being so measured as to be shorter than the length of the target mark images optimumly focused on the surface of said photodetecting means.

* * * * *